US010215845B2

(12) United States Patent
Hangauer et al.

(10) Patent No.: US 10,215,845 B2
(45) Date of Patent: Feb. 26, 2019

(54) SIMULTANEOUS RANGING AND REMOTE CHEMICAL SENSING UTILIZING OPTICAL DISPERSION OR ABSORPTION SPECTROSCOPY

(71) Applicants: Andreas Hangauer, Munich (DE); Gerard Wysocki, Princeton, NJ (US)

(72) Inventors: Andreas Hangauer, Munich (DE); Gerard Wysocki, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 308 days.

(21) Appl. No.: 15/151,812

(22) Filed: May 11, 2016

(65) Prior Publication Data

US 2016/0334507 A1 Nov. 17, 2016

Related U.S. Application Data

(60) Provisional application No. 62/159,542, filed on May 11, 2015.

(51) Int. Cl.
*G01S 7/48* (2006.01)
*G01S 17/32* (2006.01)
(Continued)

(52) U.S. Cl.
CPC ............ *G01S 7/4802* (2013.01); *G01J 3/0278* (2013.01); *G01J 3/4338* (2013.01); *G01N 21/39* (2013.01);
(Continued)

(58) Field of Classification Search
CPC .... G01N 21/39; G01N 21/31; G01N 21/3504; G01N 21/538; G01N 2021/1793;
(Continued)

(56) References Cited

U.S. PATENT DOCUMENTS 7,391,557 B1 * 6/2008 Bruch ...................... G01J 3/10
356/450
8,947,647 B2 * 2/2015 Halmos ................... G01S 17/50
356/28

(Continued)

OTHER PUBLICATIONS

Wysocki et al., "Molecular dispersion spectroscopy for chemical sensing using chirped mid-infrared quantum cascade laser" vol. 18, No. 25 / Optics Express, pp. 26123-26140, Dec. 6, 2010.

(Continued)

*Primary Examiner* — Luke D Ratcliffe
(74) *Attorney, Agent, or Firm* — Meagher Emanuel Laks Goldberg & Liao, LLP

(57) ABSTRACT

A system for simultaneous optical pathlength determination and remote chemical sensing of a sample disposed along an optical path. A modulated laser source configured for modulated light emission so that at least one spectral sideband with a sideband frequency is created, the modulated light emission is directed along the optical path and sideband frequency is varied over time. A detector is configured to detect transmitted light along the optical path and generate a detected light intensity signal. A frequency down-converter is configured to receive the detected light emission signal and generate a frequency down-converted light intensity signal. A demodulator is configured to demodulate the frequency of the down-converted light intensity signal and output an instantaneous frequency. A pathlength calculator is configured to determine an optical pathlength to the sample based on the instantaneous frequency. A frequency down-converted light intensity signal is simultaneously output for spectroscopic chemical sensing.

25 Claims, 3 Drawing Sheets

(51) Int. Cl.
   *G01S 17/95* (2006.01)
   *G01N 21/39* (2006.01)
   *G01J 3/02* (2006.01)
   *G01J 3/433* (2006.01)
   *G01N 21/17* (2006.01)
   *G01J 1/42* (2006.01)

(52) U.S. Cl.
   CPC ............ *G01S 17/325* (2013.01); *G01S 17/95* (2013.01); *G01J 2001/4242* (2013.01); *G01N 2021/1793* (2013.01); *G01N 2021/394* (2013.01)

(58) Field of Classification Search
   CPC ..... G01N 2021/1795; G01N 2021/394; G01N 2021/399; G01N 2021/4709; G01S 7/4802; G01S 17/88; G01S 17/95; G06N 99/005
   See application file for complete search history.

(56) References Cited

U.S. PATENT DOCUMENTS

| | | |
|---|---|---|
| 9,025,163 B2 | 5/2015 | Wysocki et al. |
| 2015/0159990 A1* | 6/2015 | Plusquellic .......... G01N 21/255 356/451 |
| 2016/0274025 A1* | 9/2016 | Skibo .................... G01N 21/39 |

OTHER PUBLICATIONS

Hangauer et al., "Simultaneous ranging and remote sensing utilizing chirped laser dispersion spectroscopy" In CLEO: Science and Innovations, pp. STh5C-5. Optical Society of America, 2014.

\* cited by examiner

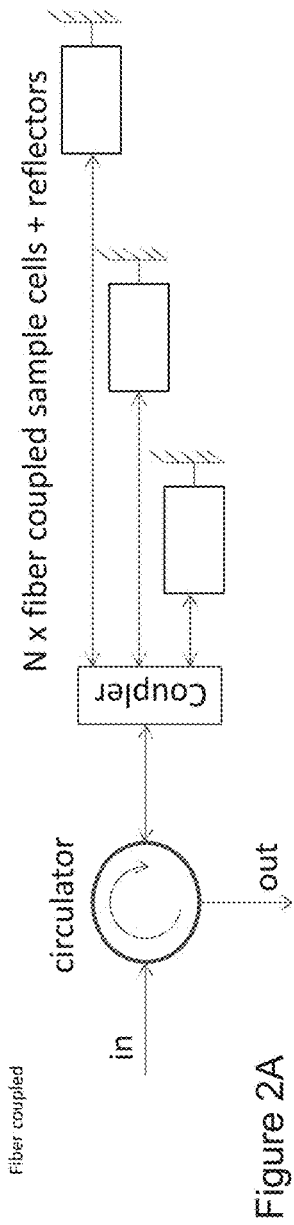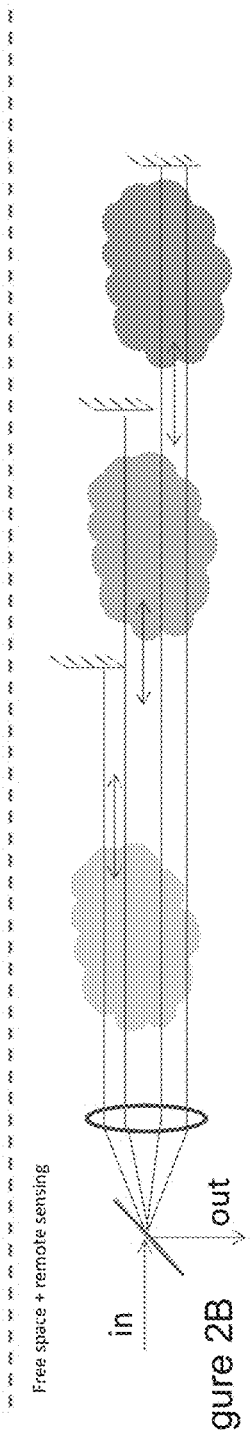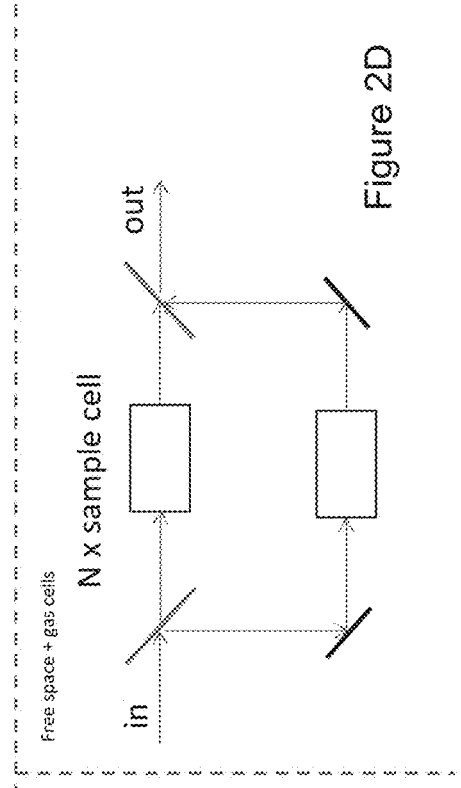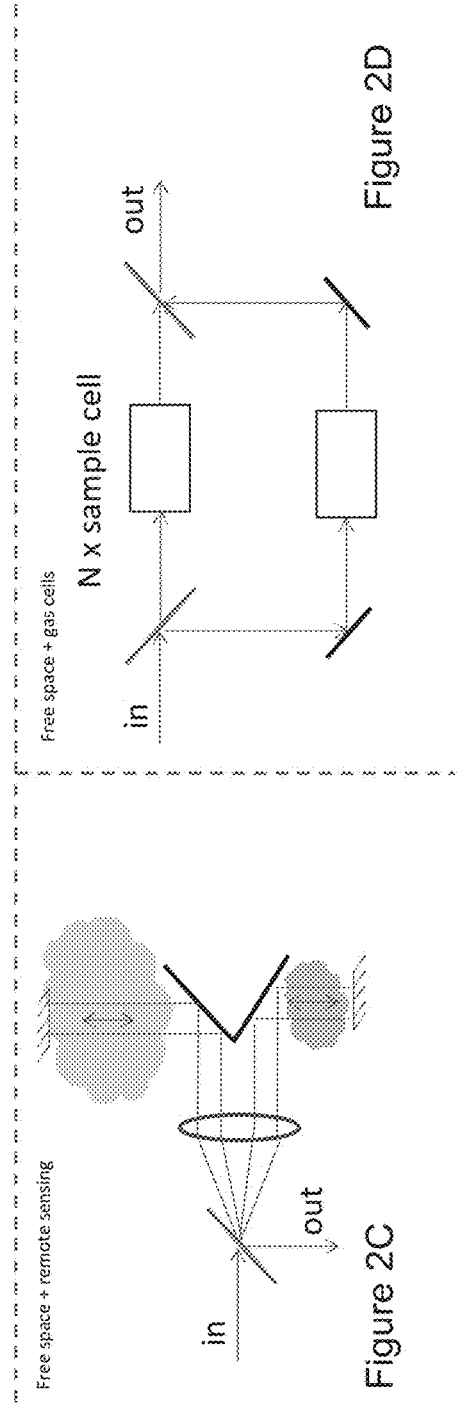
Figure 2A
Figure 2B
Figure 2C
Figure 2D

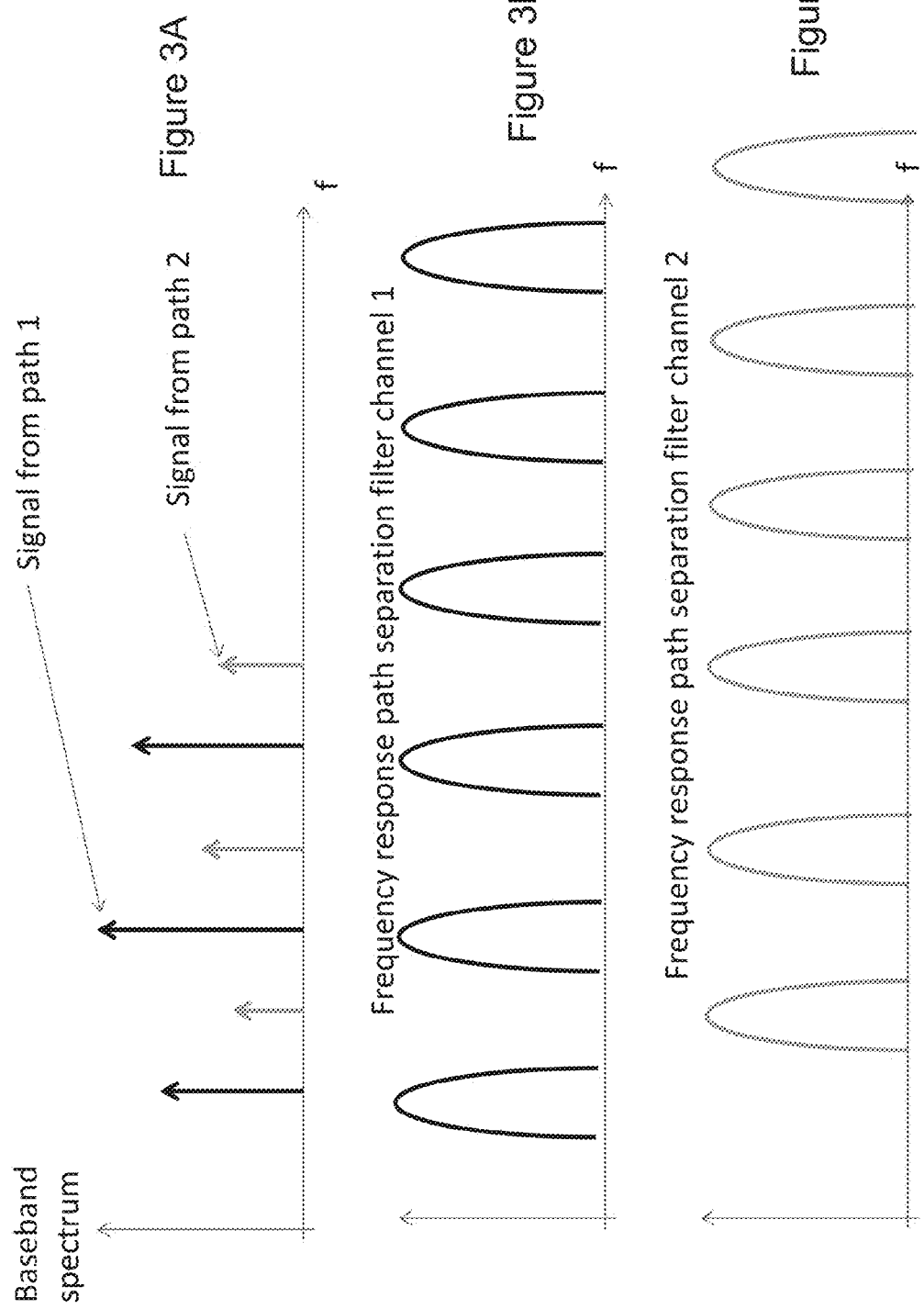

SIMULTANEOUS RANGING AND REMOTE CHEMICAL SENSING UTILIZING OPTICAL DISPERSION OR ABSORPTION SPECTROSCOPY

CROSS-REFERENCE TO PRIOR FILED APPLICATIONS

This application claims priority to U.S. provisional application 62/159,542 filed on May 11, 2015 which is incorporated herein in its entirety.

STATEMENT REGARDING FEDERALLY SPONSORED RESEARCH OR DEVELOPMENT

This invention was made with government support under Grant No. CMMI-0954897 awarded by the National Science Foundation. The government has certain rights in the invention.

FIELD OF THE INVENTION

The present disclosure generally relates to optical dispersion or absorption spectroscopy and in more particular to simultaneous ranging and remote chemical sensing in optical dispersion or absorption spectroscopy systems.

BACKGROUND

Optical dispersion spectroscopy generally measures the properties of light over a specific portion of the electromagnetic spectrum and is typically used in spectroscopic analysis to identify materials. Absorption spectroscopy is generally used to make a quantitative determination of chemical elements using the absorption of optical radiation. Typically these processes are used to determine the chemical properties of the sample. However, in most cases range information is also needed. Currently the only spectroscopic method for chemical sensing that provides simultaneous range information is the pulsed Raman LIDAR or the differential absorption LIDAR (DIAL). Both are based on pulsed laser technology and time-of-flight measurement, which requires advanced and fast measurement technology and shows limited chemical sensitivity. Improved techniques that can yield simultaneous range information along with high chemical sensitivity are needed.

SUMMARY OF THE INVENTION

A system for simultaneous optical pathlength determination and remote chemical sensing of a sample disposed along an optical path is disclosed. The system includes a modulated laser source configured for modulated light emission so that at least one spectral sideband with a sideband frequency is created, the modulated laser source being configured to direct the modulated light emission along the optical path and vary the sideband frequency over time. A detector is configured to detect transmitted light along the optical path and generate a detected light intensity signal. A frequency down-converter is configured to receive the detected light emission signal and generate a frequency down-converted light intensity signal. A demodulator is configured to demodulate the frequency of the down-converted light intensity signal and output an instantaneous frequency. A pathlength calculator is configured to determine an optical pathlength to the sample based on the instantaneous frequency. A frequency down-converted light intensity signal is simultaneously output for spectroscopic chemical sensing.

An RF signal generator may be configured to vary the sideband frequency over time. The demodulator may be a frequency demodulator configured to demodulate the frequency of the down-converted light intensity signal and output an instantaneous frequency. A path separation filter may be configured to receive the frequency down-converted light intensity signal and generate a plurality of single path frequency down-converted light intensity signals each associated with a different optical path. The path separation filter may be a comb filter. A phase corrector may be configured to correct phase variations in the frequency down-converted light intensity signal. The modulated laser source may be configured to vary the sideband frequency over time based on a piecewise linear sweep waveform. The modulated laser source may be configured to vary the sideband frequency over time based on sinusoidal wave. The modulated laser source may be configured to vary the sideband frequency over time based on a combination of a piecewise linear sweep waveform and a sinusoidal wave. The optical path may include a sample cell containing the sample. The optical path may be an open path containing the sample. Reflectors may be disposed in the open path and configured to direct the modulated light emission to the detector. The detector may be configured to detect scattered radiation from objects or particles in the open path. A spectroscopic processor may be configured to perform chemical sensing of the sample based on the frequency down-converted light emission signal.

A method for simultaneous optical pathlength determination and remote chemical sensing of a sample disposed along an optical path is also disclosed. The method includes generating a modulated laser light emission so that at least one spectral sideband with a sideband frequency is created; the modulated laser light emission having a sideband frequency that varies over time. The modulated laser light emission is directed along the optical path. A reflected light emission is detected from the optical path and a detected light intensity signal is generated. The detected light emission signal is frequency down-converted generating a frequency down-converted light intensity signal. The frequency down-converted light intensity signal is demodulated and an instantaneous frequency is output. A pathlength to the sample along the optical path is determined based on the instantaneous frequency. The frequency down-converted light emission is output for spectroscopic chemical sensing.

An RF signal generator may be provided to vary the sideband frequency over time. A light intensity signal from the detector is frequency may be down-converted by a down-converter synchronized with the generated sideband frequency. The frequency down-converted light intensity signal may be frequency demodulated. The frequency down-converted light emission signal may be filtered to generate a plurality of single path frequency down-converted light intensity signals each associated with a different path. A comb filter may be provided to generate the plurality of single path frequency down-converted light intensity signals. Phase variations in the frequency down-converted light intensity signal may be corrected. The sideband frequency may be varied over time based on a piecewise linear sweep waveform. The sideband frequency may be varied over time based on a sinusoidal wave. The sideband frequency may be varied over time based on a combination of a piecewise linear sweep waveform and a sinusoidal wave. A spectroscopic processor may be provided to perform chemical sensing of the sample based on the frequency down-converted light intensity signal.

BRIEF DESCRIPTION OF THE FIGS.

FIG. 2A is a block diagram showing how multiple paths can be realized with a fiber based configuration;

FIG. 2B is a block diagram showing how multiple paths can be realized in free space;

FIG. 2C is a block diagram showing an example configuration using a beam splitter to allow multiple paths to be realized in free space;

FIG. 2D is a block diagram showing a configuration with multiple sample cells configured to allow multiple paths to be realized in free space;

FIG. 3A is a graph showing signals from multiple paths;

Figure 1:
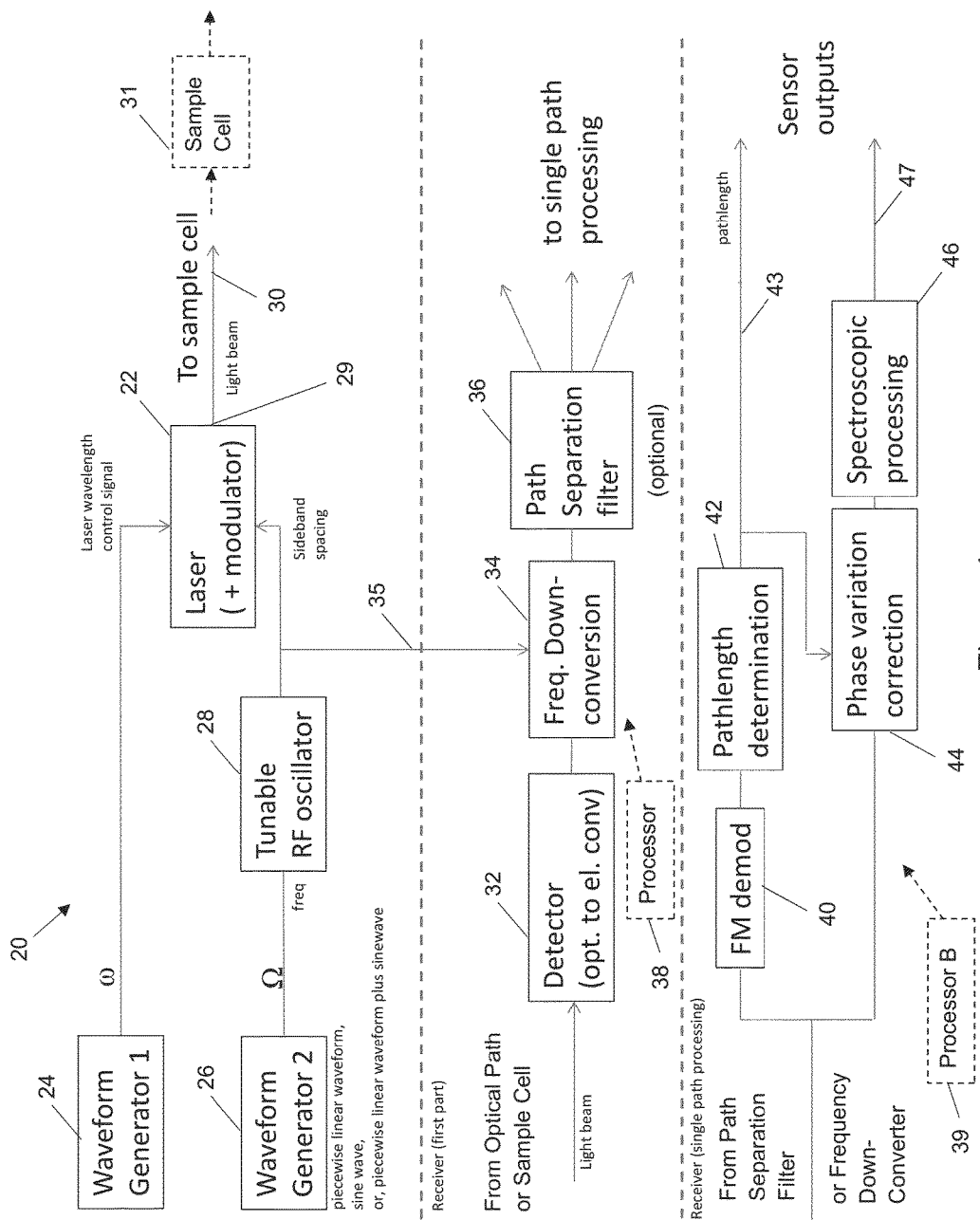
FIG. 1 is a block diagram of a spectroscopic system configured for simultaneous ranging and remote chemical sensing.

FIG. 3B is a graph showing the frequency response of a path separation filter used to filter signals in channel 1 (path 1 in FIG. 3A); and FIG. 3C is a graph showing the frequency response of a path separation filter used to filter signals in channel 2 (path 2 in FIG. 3A).

DETAILED DESCRIPTION

Disclosed herein is a process for simultaneous ranging and remote chemical sensing utilizing optical dispersion or absorption spectroscopy. The disclosed approach enables new capabilities in established technologies used for laser spectroscopic chemical sensing such as chirped laser dispersion spectroscopy (CLaDS, Wysocki et al., Princeton University), frequency modulation (FM) spectroscopy or wavelength modulation spectroscopy (WMS).

The disclosed approach enables simultaneous ranging and a molecular detection, a combination of capabilities that was not possible to achieve with current state-of-the art continuous wave laser based spectrometers. Since every application of molecular detection needs pathlength normalization, a capability of simultaneous range measurement strongly enhances the utility of chemical sensing. This technology is especially beneficial to remote and open path chemical sensing as well as closed-path sensing applications that utilize multi-mode/scattering-based gas cells for which the pathlength is not known a-priori (e.g. integrating spheres).

Potentially addressable multi-path chemical sensing for tomographic chemical detection with a single laser-based instrument has a potential to greatly reduce the total cost for a sensing infrastructure. Capabilities of conventional spectrometers based on e.g. CLaDS, FM spectroscopy or WMS can be significantly enhanced by implementing the technology disclosed here.

As explained above, the only spectroscopic method for chemical sensing that provides simultaneous range information is the pulsed Raman LIDAR or the differential absorption LIDAR (DIAL). Both are based on pulsed laser technology and time-of-flight measurement, which requires advanced and fast measurement technology and shows limited chemical sensitivity.

The disclosed approach uses a continuous wave that allows for simultaneous molecular sensing and ranging. It has high chemical sensitivity (because it is a continuous wave approach) and provides knowledge of the optical pathlength, which is an important feature in remote sensing applications.

In non-remote sensing applications, knowledge of the optical pathlength simplifies the calibration. Additionally, system reliability can be improved through monitoring of the optical pathlength. Unintended changes to the optical pathlength can be monitored (e.g. accidental obstruction of optical path, or additional unwanted reflections from contamination), which is not possible with any of the presently available technologies. This is of particular use in case of optical gas cells, which have unknown or undefined effective optical pathlength, such as integrating spheres, non-resonant optical cavities, or solid-state scattering-based diffusion gas cells. Presently there is no technical solution that could address a problem of slowly drifting effective optical pathlength simultaneous with the spectroscopic detection. Since such cells are low cost and can be manufactured and aligned easily, which significantly reduces total sensor cost, the disclosed method can serve as viable chemical detection scheme with active pathlength monitoring.

Tomographic gas plume monitoring techniques require simultaneous multipath measurement using a single laser and detector. The capability of simultaneous pathlength measurement could easily address any complex multipath systems. Moreover tomographic measurements with dynamically moving targets (e.g. mobile retroreflector mounted on UAV) require truly continuous pathlength measurement, which can be uniquely addressed with this technology. No other continuous wave spectroscopic method can provide similar functionality.

Another application of this technology can be realized with multiple cascaded sensors (measurement cells) in one optical train. The path difference between cascaded sensor heads can be clearly resolved with the disclosed technology. Besides simultaneous detection of spectroscopic information and path length, also the simultaneous detection and separation of measurement signals from multiple paths of different length in the optical path can be resolved. Applications for line-distributed sensors based on cascaded systems are multiple such as for buildings, pipeline monitoring etc. An advantage of utilization of multiple paths/sensors is that only one laser and detector are needed and hence the total sensor complexity and cost is reduced. Also the common problem of using a reference cell with a gas reference or a reference etalon or both can be implemented in the same optical train with just one laser and one detector as long as those signals can be separated based on different optical path length to these elements of the optical train.

The disclosed encompasses systems, methods and processes. A general description is provided herein. A specific implementation example and experimental demonstration is also disclosed in the paper appended in U.S. Provisional Application 62/159,542 filed on May 11, 2015 (A. Hangauer and G. Wysocki, "Simultaneous ranging and remote sensing utilizing chirped laser dispersion spectroscopy," in CLEO: 2014 Postdeadline Paper Digest, OSA Technical Digest (online) (Optical Society of America, 2014), paper STh5C.5.) both of which are incorporated by reference in their entirety.

The primary implementation is based on a frequency-chirped RF carrier, but alternatively a chirp of the optical frequency followed by a heterodyne or homodyne detection can also be used. The experimental setup will differ for both configurations but both share the same fundamental detection principle and require similar data processing. The description below focuses on the chirped RF carrier approach. One aspect of the disclosed approach is that through application of specially chosen waveforms and dedicated signal processing conventional spectroscopic systems can be upgraded with the new functionality offered by the disclosed approach (i.e. range measurement).

FIG. 1 is a block diagram of a spectroscopic system 20 configured for simultaneous ranging and remote chemical sensing. The system includes a modulated laser source shown generally by block 22. The modulated laser source 22 is configured for modulated light emission (either by injection current modulation or applying an external modulator) so that spectral sidebands are created. In this example a first waveform generator 24 is configured control the fundamental optical frequency $\omega$ generated by the laser. The output of the first waveform generator 24 is coupled to an input of the modulated laser source 22. A second waveform generator 26 is configured to control the modulation frequency $\Omega$. The output of the second waveform generator 26 is coupled to an input of the tunable radio-frequency (RF) oscillator 28 that generates electrical RF waveform with frequency $\Omega$. This RF waveform is coupled to an input of the modulated laser source 22. The resulting modulated laser output 29 is generally configured for modulated light emission at fundamental frequency $\omega$ with one or more spectral sidebands separated by $\Omega$ from the fundamental frequency 107. The modulated laser output 29 is directed along an optical path 30. It should be understood that the term optical path encompasses an open path as well as a path that includes a sample cell shown generally by block 31. In this example, the modulated laser output 29 is generally directed into a sample cell shown generally by block 31. The reflected light beam is then detected by a detector (optical to electrical signal conversion) shown generally by block 32 to generate a signal (electrical signal) proportional to detected light intensity. Processing of the detected light intensity signal is carried out by processor(s) as generally shown by block 38

The sideband spacing is defined by the frequency of RF oscillator 28. The number of sidebands or their relative strength is not important for the disclosed method and a property of the laser/modulator used to create the sidebands. This implementation is generally based on an experimental setup based on CLaDS (either AOM, EOM or direct modulation based), but wavelength or frequency modulation spectroscopy systems could also be used. The laser should also be tunable and the waveform used for tuning can be chosen appropriately (the waveform itself is not important for the method to work, but a few important examples are outlined below).

An important element of the disclosed approach is the operation of the RF oscillator 28 with time varying frequency. There at least three different ways of time variation that may be used. A piecewise linear sweep waveform (such as a ramp or triangle wave) or a sinusoidal wave or a sum of both of these two (in any case at least one of the mentioned waveforms is present, so there is a continuous or non-discrete variation in any case). Typically, but not necessarily, the imposed variation of frequency is small compared to the constant frequency offset. If multiple paths are to be resolved, the waveform should possess either a triangle or ramp like waveform (plus the mentioned offset), the additional sine wave may be present to enhance the resolution, but may not be necessary when very long paths are to be probed.

Another aspect of the disclosed approach is that the received signal is frequency down-converted using a reference signal derived from the modulating RF oscillator 28, which assures the same variation in frequency $\Omega$. This is generally shown by block 34 discussed in more detail below. In general, the frequency down-converter 34 is configured to receive the detected light emission signal from the sample cell and generate a down-converted light intensity signal. As generally shown by arrow 35, the down-conversion is done with the same variation in frequency (determined at RF oscillator 28), which is necessary for the approach to work. This down-conversion produces a complex baseband signal, which is now subject to further processing. Alternatively, the frequency used for demodulation might have a constant frequency-offset compared to the frequency $\Omega$ used for optical sideband generation (but its temporal variation is the same, besides the offset). This is to realize detection at an intermediate frequency (IF), which may simplify processing. In that case a second conversion step realizing the conversion from IF to the complex baseband (zero frequency) is done afterwards (preferably in the digital domain). So both approaches finally produce the same complex baseband signal.

A third aspect of the disclosed approach is the path separation filter 36 which is described below and which enables multi-path sensing, a unique capability not provided by any other known spectroscopic system or method known to date. The path separation filter 36 is configured to receive the frequency down-converted light emission signal and generate a plurality of single path frequency down-converted light emission signals each associated with a different path. The linear chirp of the carrier frequency (with either ramp or triangle temporal variation) causes a frequency shift of the received baseband signal. When the sample cell contains multiple paths of different length, one gets multiple copies of the signal one expects from a single path but with different frequency shifts. The path separation filter separates these spectral components, which essentially allows for a multi-path measurement. After the separation the individual spectral components are processed separately by plurality of processors) B shown generally by block 39. Each Processor B analyzes data from a single path measurement. FIG. 2A is a block diagram showing how multiple paths can be realized with a fiber based configuration. FIG. 2B is a block diagram showing how multiple paths can be realized in free space.

FIG. 2C is a block diagram showing another configuration using a beam splitter to allow multiple paths to be realized in free space. FIG. 2D is a block diagram showing a configuration with multiple sample cells configured to allow multiple paths to be realized in free space. Range (or optical path) measurement is done for each path individually using Processor B shown as 39 in FIG. 1. An important point is that paths which are different in length can be separated and the amount of absorption and dispersion from the molecular transitions is separated in an ideal way. In case only a single path is present the pathlength separation filter 36 may be omitted.

Another aspect of the disclosed approach is the Processor B 39 that contains both the pathlength determination branch and spectroscopic processing branch. The pathlength determination branch contains FM demodulator, e.g. as shown generally by block 40, and a pathlength calculator e.g. as shown generally by block 42. The spectroscopic processing branch contains phase variation correction, e.g., as shown generally by block 44, and spectroscopic processing, e.g., as shown generally by block 46, as described below. The spectroscopic processing (block 46) may be done analogously to the processing known from existing spectroscopic methods, such as CLaDS, frequency modulation spectroscopy or wavelength modulation spectroscopy. In case of CLaDS the phase correction is not needed and the output of the FM demodulator signal (what is used as input to the pathlength determination) can be re-used to perform the CLaDS spectroscopic evaluation. This produces an especially economical processing. This processing may include lock-in detection for chirp modulated CLaDS. This special case is described in detail in the attached paper. In any case the spectroscopic information may be determined from the phase or the amplitude of the phase corrected baseband signal, when the central laser emission wavelength is regarded as the signals x-axis. For that the laser wavelength is typically tuned slowly around the spectral feature of interest. With theoretical description of the recorded signals, the gas parameters such as range integrated concentration, pressure and temperature can be extracted by either fitting to a theoretical model or comparison with experimental reference spectra. As mentioned earlier an addition sinusoidal wavelength modulation may be present in addition to enhance sensitivity. In that case, line locking may be also used so that the slow wavelength scanning ramp can be spared. With this additional sine wave modulation typically a lock-in detection of the absolute value of the real part of the phase corrected or the absolute value of the signal is employed. If sinusoidal modulation of both the wavelength and the sinusoidal carrier frequency are used simultaneously, it is advantageous that the one is an integer multiple or an integer divisor of the other. This is to simplify the pathlength separation filter 36, and makes the signal from the optical pathlength and the one of the spectroscopic interaction appear in different order harmonics.

1. Path Separation Filter:

The linear sweep of the carrier frequency provides a shift of the baseband spectrum proportional to the length of the corresponding path. Different paths produce different shift in the baseband signal. The frequency shift is given by the linear carrier chirp rate (unit Hz/sec) times the total group delay of the relevant path.

In case of an additional sinusoidal modulation on either the laser emission wavelength or the carrier frequency, the baseband signal of a single path comprises a multitude of lines with spacing corresponding to this modulation frequency. Hence by choosing the RF chirp rate and modulation frequencies appropriately one can always achieve that the spectra are not overlapping in frequency domain. If the shift from the chirp is smaller than the spacing of the lines, path separation filter 36 may be implemented with a comb filter. A comb filter will serve as separation for the individual components from different optical paths. The comb filter for each path is the same, but contains a frequency shift operation before and with inverse direction after filtering to realize the different offset frequencies of the filter.

FIG. 3A is a graph showing signals from multiple paths. FIG. 3B is a graph showing the frequency response of a path separation filter used to filter signals in channel 1 (path 1 in FIG. 3A). FIG. 3C is a graph showing the frequency response of a path separation filter used to filter signals in channel 2 (path 2 in FIG. 3A). In case of frequency shift much larger than the total bandwidth of the whole spectrum, ordinary bandpass filters can be used instead. The filter bandwidth for both cases will be fixed and selected according to the minimum optical pathlength difference (which sets the minimum difference of the frequency shifts from each path). It should be wide enough to capture the (small) time variation of the individual components, since these contain the information about the spectroscopic quantities, but as small as possible to provide highest selectivity between paths. The shift offset for each of the filters will be chosen adaptively according to the pathlengths expected. Alternatively, a coarse spectral correlation step with a pre-recorded or pre-calculated spectrum corresponding to a zero length optical path may be used to extract the number paths and each of their frequency shifts. During operation, a control algorithm with a feedback from the determined pathlengths may be used to slowly adjust the separation filter offsets appropriately. Note that the frequency offsets of the filters do not need to match the spectral shift exactly, since the filters should only separate the different paths. The evaluation of paths is done later. The offsets may be chosen in such a way that the filters will not overlap and preferably the zeros of the filters frequency response are placed at frequency points where the strong signals from the other paths are located. In case that is not possible, the RF chirp modulation frequency (i.e. the spacing of baseband components) or the linear RF chirp rate may be adjusted so that the conditions are met in a best possible way.

2. Pathlength Determination:

After path separation (block 36) and FM demodulation (block 40), the instantaneous frequency (which is the output signal after FM demodulation) is used for determination of the path length as shown generally by pathlength calculator 42. If there is no sinusoidal chirp of the RF frequency, the time averaged value of the FM divided by the linear RF chirp rate and divided by speed of light gives the total optical path length. From a reference measurement it is known how much the electronics including cables and filters contribute to this value. This known offset is subtracted from the value to obtain the true optical path length.

In case of a sinusoidal modulation of the RF carrier frequency, lock-in detection is done at the frequency of this sinusoidal modulation. This gives the variation amplitude of the FM, which analogously to the above formula gives the path length. The advantage of sinusoidal modulation compared to a linear RF chirp only is that higher pathlength resolution is obtained, since higher effective chirp rates are possible. To be able to resolve several paths, a linear RF chirp component is needed. In case of a single path a sinusoidal modulation alone is sufficient.

If in case the laser wavelength is also sinusoidally modulated, additional frequency components may exist (at multiples of the relevant modulation frequency) which contain the spectroscopic information. In case it is an integer divisor or integer multiple of the RF chirp modulation frequency, the pathlength may appear as an offset to the spectroscopic spectra. However, since the spectroscopic information appears as a distinct feature in the signals (when the wavelength from slow scanning is regarded as x-axis) this information also be separated in an ideal sense.

Sinusoidal modulation has also the advantage of being capable of measuring the speed of the reflecting target. The speed of the target is proportional to the Doppler shift, which makes the received FM non sinusoidal and cause a second order or higher order harmonic in the FM. Hence the second harmonic at multiple at the RF carrier modulation frequency will be proportional to the target speed.

3. Phase Correction and Spectroscopic Processing

Once the pathlength is determined, a phase correction is employed as shown generally by block 44. In this step the theoretically expected frequency variation (those observed in the FM demodulation) is synthetically calculated and used to phase back shift the baseband signal. Hence the signal contributions and frequency shift caused from a nonzero pathlength are removed. This necessary synthetic signal is either a constant tone or a sinusoidal FM wave which parameters only depend on the optical pathlength and the ideally known RF chirp parameters.

After this back-shift the complex baseband signal is obtained which can be processed according to known spectroscopic processing algorithms, e.g. CM-ClaDS demodulation or simple wavelength demodulation as generally shown by block 46.

The ranging may also be implemented by beating the two chirped optical waves directly with each other without the need for RF carrier chirp. In this case also an additional sinusoidal wavelength modulation is present, the frequency of this modulation is fixed (i.e. the modulation frequency is not chirped). The signal demodulation can be performed using heterodyne or homodyne detection with one or two lasers.

There is no known continuous wave spectroscopic method so far that provides simultaneous measurement of the optical pathlength. Also the achievable resolution in cascaded sensor systems is not known at this time. For open path remote sensing the disclosed approach provides a simultaneous absolute optical pathlength measurement, which in turn allows calculating the average gas concentration. Manual determination of pathlength is not necessary and is provided by the instrument.

Gas tomography in irregularly shaped environments is possible with the disclosed approach, without need for separate ranging instrument. Monitoring of gas plumes or emission from the ground can be realized including static and dynamic multi-path tomographic measurements.

Integrating spheres or non-resonant cavities are cost efficient, and can be used as gas cells with the disclosed approach that provides effective path measurement. Cascaded sensor systems have applications in buildings or along pipelines where a single source and detector are combined with multiple measurement cells. Presently for each measurement point a separate sensor has to be used, so the overall complexity is significantly reduced.

As mentioned above, the disclosed approach may be employed in Chirped Laser Dispersion Spectroscopy to provide for multi path remote sensing, and may be employed in methane remote sensing instruments, which would have significantly enhanced usefulness in the field with the ranging capability provided by the disclosed approach.

Further description of the disclosed process and system is included in U.S. provisional application 62/159,542 filed May 11, 2015 and its appendix which are incorporated by reference in their entirety as if fully set forth herein. In addition, the references listed herein and all references listed in U.S. provisional application 62/159,542 filed May 11, 2015 and its appendix are also part of the application and are incorporated by reference in their entirety as if fully set forth herein.

It should be understood that many variations are possible based on the disclosure herein. Although features and elements are described above in particular combinations, each feature or element can be used alone without the other features and elements or in various combinations with or without other features and elements. The digital processing techniques disclosed herein may be partially implemented in a computer program, software, or firmware incorporated in a computer-readable (non-transitory) storage medium for execution by a general-purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general-purpose processor, a special purpose processor, a conventional processor, a digital signal processor (DSP), a plurality of microprocessors, one or more microprocessors in association with a DSP core, a controller, a microcontroller, Application-Specific Integrated Circuits (ASICs), Field-Programmable Gate Arrays (FPGAs) circuits, any other type of integrated circuit (IC), and/or a state machine.

What is claimed is:

1. A system for simultaneous optical pathlength determination and remote chemical sensing of a sample disposed along an optical path, the system comprising:
    a modulated laser source configured for modulated light emission so that at least one spectral sideband with a sideband frequency is created, the modulated laser source being configured to direct the modulated light emission along the optical path, the modulated laser source being configured to vary the sideband frequency over time;
    a detector configured to detect transmitted light from the optical path and generate a detected light intensity signal;
    a frequency down-converter configured to receive the detected light intensity signal and generate a frequency down-converted light intensity signal;
    a demodulator configured to demodulate the frequency of the down-converted light intensity signal and output an instantaneous frequency;
    a pathlength calculator configured to determine an optical pathlength to the sample based on the instantaneous frequency; and
    the frequency down-converted light intensity signal being simultaneously output for spectroscopic chemical sensing.

2. The system of claim 1, further comprising an RF signal generator configured to vary the sideband frequency over time.

3. The system of claim 1, wherein the demodulator is a frequency demodulator configured to demodulate the frequency of the down-converted light intensity signal and output an instantaneous frequency.

4. The system of claim 1, further comprising a path separation filter configured to receive the frequency down-converted light intensity signal and generate a plurality of single path frequency down-converted light intensity signals each associated with a different optical path.

5. The system of claim 4 wherein the path separation filter is a comb filter.

6. The system of claim 1 further comprising a phase corrector configured to correct phase variations in the frequency down-converted light intensity signal.

7. The system of claim 1 wherein the modulated laser source is configured to vary the sideband frequency over time based on a piecewise linear sweep waveform.

8. The system of claim 1 wherein the modulated laser source is configured to vary the sideband frequency over time based on a sinusoidal wave.

9. The system of claim 1 wherein the modulated laser source is configured to vary the sideband frequency over time based on a combination of a piecewise linear sweep waveform and a sinusoidal wave.

10. The system of claim 1 wherein the optical path includes a sample cell containing the sample.

11. The system of claim 1 wherein the optical path is an open path containing the sample.

12. The system of claim 11 further comprising reflectors in the open path configured to direct the modulated light emission to the detector.

13. The system of claim 11 wherein the detector is configured to detect scattered radiation from objects or particles in the open path.

14. The system of claim 1 further comprising a spectroscopic processor configured to perform chemical sensing of the sample based on the frequency down-converted light intensity signal.

15. A method for simultaneous optical pathlength determination and remote chemical sensing of a sample disposed along an optical path, the method comprising:

Generating a modulated laser light emission so that at least one spectral sideband with a sideband frequency is created; the modulated laser light emission having a sideband frequency that varies over time, directing the modulated laser light emission along the optical path;

detecting a reflected light emission from the optical path and generating a detected light intensity signal;

frequency down-converting the detected light intensity signal and generating a frequency down-converted light intensity signal;

demodulating the frequency down-converted light intensity signal and outputting an instantaneous frequency;

determining a pathlength to the sample based on the instantaneous frequency; and outputting the frequency down-converted light intensity signal for spectroscopic chemical sensing.

16. The method of claim 15, further comprising providing an RF signal generator configured to vary the sideband frequency over time.

17. The method of claim 15, wherein a light intensity signal from the detector is frequency down-converted by a down-converter synchronized with the generated sideband frequency.

18. The method of claim 15, wherein the frequency down-converted light intensity signal is frequency demodulated.

19. The method of claim 15, further comprising filtering the frequency down-converted light intensity signal and generating a plurality of single path frequency down-converted light intensity signals each associated with a different path.

20. The method of claim 19, further comprising providing a comb filter to generate the plurality of single path frequency down-converted light intensity signals.

21. The method of claim 15, further comprising correcting phase variations in the frequency down-converted light intensity signal.

22. The method of claim 15, further comprising varying the sideband frequency over time based on a piecewise linear sweep waveform.

23. The method of claim 15, further comprising varying sideband frequency over time based on a sinusoidal wave.

24. The method of claim 15, further comprising varying the sideband frequency over time based on a combination of a piecewise linear sweep waveform and a sinusoidal wave.

25. The method of claim 15, further comprising providing a spectroscopic processor configured to perform chemical sensing of the sample based on the frequency down-converted light intensity signal.

* * * * *